US00PP18957P2

(12) United States Plant Patent
Zaias Fast

(10) Patent No.: US PP18,957 P2
(45) Date of Patent: Jun. 17, 2008

(54) ***CODIAEUM* PLANT NAMED 'REVOLUTIONS'**

(50) Latin Name: *Codiaeum variegatum*
Varietal Denomination: Revolutions

(76) Inventor: Magaly Zaias Fast, 11068 Northwest 3rd St., Coral Springs, FL (US) 33071

( * ) Notice: Subject to any disclaimer, the term of this patent is extended or adjusted under 35 U.S.C. 154(b) by 0 days.

(21) Appl. No.: 11/716,412

(22) Filed: Mar. 9, 2007

(51) Int. Cl.
*A01H 5/00* (2006.01)

(52) U.S. Cl. ..... Plt./373

(58) Field of Classification Search ..... Plt./373
See application file for complete search history.

*Primary Examiner*—Kent Bell
*Assistant Examiner*—S. B. McCormick-Ewoldt

(57) ABSTRACT

A new cultivar of *Codiaeum* plant named 'Revolutions' that is characterized by tightly curled variegated leaves.

1 Drawing Sheet

Botanical classification: *Codiaeum variegatum.*
Variety denomination: 'Revolutions'.

BACKGROUND OF THE INVENTION

The present invention relates to a new and distinct cultivar of *Codiaeum* plant botanically known as *Codiaeum variegatum* and hereinafter referred to by the cultivar name 'Revolutions'.

The new cultivar was discovered by the inventor in a cultivated area of Puerto Rico in 1989. 'Revolutions' was discovered as a naturally occurring branch mutation of *Codiaeum variegatum* 'Rams Horns' (not patented).

Asexual reproduction by terminal cuttings of the new cultivar 'Revolutions' was first performed in 1989 Puerto Rico. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Codiaeum* cultivar 'Revolutions'.

1. *Codiaeum* 'Revolutions' exhibits tightly curled variegated leaves.

The closest comparison cultivar is the parent plant *Codiaeum* 'Rams Horns'. The new cultivar 'Revolutions' is distinguishable from 'Rams Horns' by the following characteristics:

1. 'Revolutions' has leaves with more curls than 'Rams Horns'.
2. 'Revolutions' has leaves with curls that are tighter than 'Rams Horns'.

BRIEF DESCRIPTION OF THE DRAWING

The accompanying photograph illustrates the distinguishing traits of *Codiaeum* 'Revolutions'. The plant in the photograph shows an overall view of a 50 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Codiaeum* cultivar named 'Revolutions'. Data was collected in Evergem, Belgium from 50 week old greenhouse grown plants in 13 cm containers. The time of year was Fall and the average temperature range was 22-32 degrees Centigrade during the day and 12-22 degrees Centigrade at night. No photoperiodic treatments or growth retardants were used. Color determinations are in accordance with The Royal Horticultural Society Colour Chart 2001 edition, except where general color terms of ordinary dictionary significance are used. The growing requirements are similar to the species. 'Revolutions' has not been tested under all possible conditions and phenotypic differences may be observed with variations in environmental, climatic, and cultural conditions, however, without any variance in genotype.

Botanical classification: *Codiaeum variegatum* 'Revolutions'.
Use: Ornamental.
Parentage: 'Revolutions' is a naturally occurring branch mutation of *Codiaeum* 'Rams Horns'.
Vigor: Low to moderate.
Growth rate: 5 cm. per month.
Growth habit: Upright.
Plant shape: Narrow inverted triangle.
Suitable container size: 10.5 cm. diameter container.
Height: Average 18.4 cm in height.
Width: Average 10.3 cm in width.
Hardiness: USDA Zone 10.
Propagation: Terminal cuttings.
Time to produce a rooted cutting: Approximately 7 days in Summer at 27° C. and 10-14 days in Winter at 20° C.
Time to produce a young plant: Approximately 21 days in Summer at 27° C. and 28 days in Winter at 20° C.
Root system: Fine and fibrous.
Stem:
*Pinching required.*—Yes.
*Number of lateral branches.*—Average 1.
*Lateral branch length.*—2.1 cm.
*Lateral branch diameter.*—2 mm.
*Internode length.*—1.4 cm.
*Stem shape.*—Rounded and moderately glossy.

*Stem strength.*—Strong.

*Stem color.*—143 A to 143B to 154C to 154D.

Foliage:

*Texture.*—Glossy.

*Leaf arrangement.*—Alternate.

*Compound or single.*—Single.

*Leaf shape.*—Narrow oblong.

*Leaf apex.*—Acute.

*Leaf base.*—Truncate.

*Leaf length.*—Average 11.5 cm.

*Leaf width.*—2.3 cm in width.

*Quantity of leaves per main stem.*—Average 15.

*Pubescence.*—No leaf pubescence.

*Leaf margin.*—Entire, very undulate.

*Vein pattern.*—Pinnate; only the main vein is visible.

*Young leaf color* (*upper surface*).—143B, occasionally with small dots or central variegation and dots N144B.

*Young leaf color* (*lower surface*).—144A, occasionally the central variegation on the upper side, along with the main vein, is slightly visible, 144B.

*Mature leaf color* (*upper surface*).—139A, occasionally with small dots, 1 mm. diameter, or central variegation, along with the main vein, slightly visible, 144B.

*Mature leaf color* (*lower surface*).—137C to 138A, occasionally the small dots on the upper side are visible, 145C; central variegation on the upper side, along with the main vein are also visible, 12A to 12B.

*Vein color* (*upper surface*).—145A to 12B.

*Vein color* (*lower surface*).—144B to 144C to 12B.

*Leaf attachment.*—Petiolate.

*Petiole dimensions.*—Average 1.2 cm in length and 1.5 mm in diameter.

*Petiole aspect.*—Glossy.

*Petiole surface.*—Smooth, glossy.

*Petiole color.*—144A to 151C to 151D.

*Durability of foliage to stress.*—Moderate to high.

*Other characteristics.*—Leaves relatively leathery, extremely curved and moderately crinkled.

Flowers: Flowers have not been observed.

Disease and insect resistance: Plants of the new *Codiaeum* have not been observed for disease or insect resistance.

What is claimed is:

1. A new and distinct variety of *Codiaeum* plant named 'Revolutions' as described and illustrated.

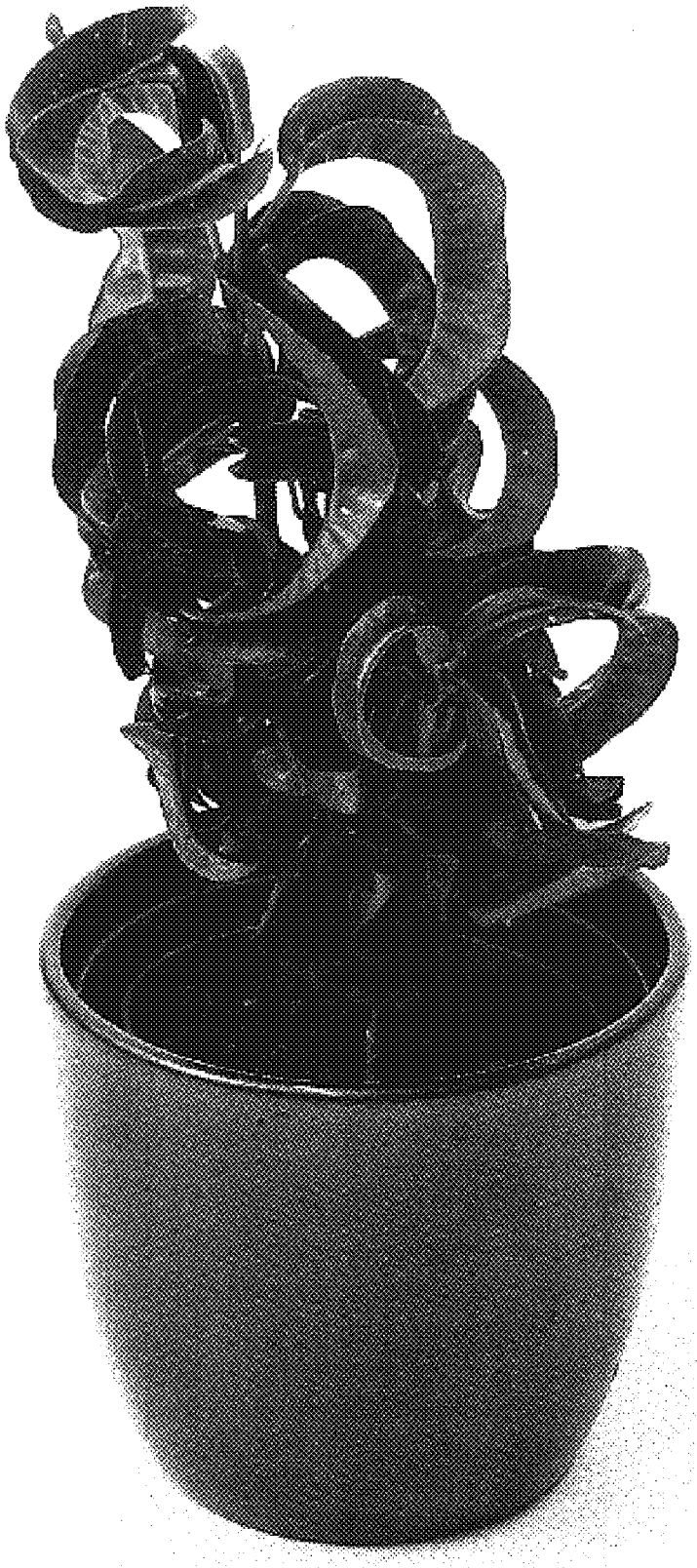

* * * * *